United States Patent
Chen et al.

(10) Patent No.: US 7,910,778 B2
(45) Date of Patent: *Mar. 22, 2011

(54) PROCESS FOR PRODUCING CYCLOHEXYLBENZENE

(75) Inventors: Tan-Jen Chen, Kingwood, TX (US); John Scott Buchanan, Lambertville, NJ (US); Jane Chi-ya Cheng, Bridgewater, NJ (US); Terry E. Helton, Bethlehem, PA (US)

(73) Assignee: ExxonMobil Chemical Patents Inc., Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 12/665,154

(22) PCT Filed: Jul. 11, 2008

(86) PCT No.: PCT/EP2008/006072
§ 371 (c)(1),
(2), (4) Date: Dec. 17, 2009

(87) PCT Pub. No.: WO2009/021604
PCT Pub. Date: Feb. 19, 2009

(65) Prior Publication Data
US 2010/0191017 A1    Jul. 29, 2010

Related U.S. Application Data

(60) Provisional application No. 60/964,874, filed on Aug. 15, 2007.

(51) Int. Cl.
C07C 45/27 (2006.01)
C07C 27/08 (2006.01)
C07C 2/68 (2006.01)
C07C 15/067 (2006.01)

(52) U.S. Cl. ......... 568/361; 568/798; 585/446; 585/467

(58) Field of Classification Search ................... 568/361, 568/798; 585/446, 467
See application file for complete search history.

(56) References Cited

U.S. PATENT DOCUMENTS

| | | |
|---|---|---|
| 3,412,165 A | 11/1968 | Slaugh et al. |
| 3,760,017 A * | 9/1973 | Arkell et al. ................. 585/268 |
| 3,760,018 A | 9/1973 | Suggitt et al. |
| 3,760,019 A | 9/1973 | Crone, Jr. et al. |
| 3,784,617 A | 1/1974 | Suggitt et al. |
| 3,784,618 A | 1/1974 | Suggitt et al. |
| 3,839,477 A | 10/1974 | Suggitt et al. |
| 3,864,421 A | 2/1975 | Suggitt |
| 3,957,687 A | 5/1976 | Arkell et al. |
| 4,021,490 A | 5/1977 | Hudson |
| 4,094,918 A | 6/1978 | Murtha et al. |
| 4,122,125 A | 10/1978 | Murtha et al. |
| 4,152,362 A | 5/1979 | Murtha |
| 4,177,165 A | 12/1979 | Murtha et al. |
| 4,206,082 A | 6/1980 | Murtha et al. |
| 4,219,689 A | 8/1980 | Murtha |
| 4,268,699 A | 5/1981 | Murtha et al. |
| 4,329,531 A | 5/1982 | Murtha et al. |
| 4,439,409 A | 3/1984 | Puppe et al. |
| 4,447,554 A | 5/1984 | Murtha et al. |
| 4,826,667 A | 5/1989 | Zones et al. |
| 4,954,325 A | 9/1990 | Rubin et al. |
| 5,053,571 A | 10/1991 | Makkee |
| 5,146,024 A | 9/1992 | Reed |
| 5,236,575 A | 8/1993 | Bennett et al. |
| 5,250,277 A | 10/1993 | Kresge et al. |
| 5,334,795 A | 8/1994 | Chu et al. |
| 5,362,697 A | 11/1994 | Fung et al. |
| 5,557,024 A | 9/1996 | Cheng et al. |
| 6,037,513 A | 3/2000 | Chang et al. |
| 6,077,498 A | 6/2000 | Diaz Cabanas et al. |
| 6,489,529 B1 * | 12/2002 | Cheng et al. ................... 585/471 |
| 6,506,953 B1 * | 1/2003 | Cheng et al. ................... 585/269 |
| 6,730,625 B1 * | 5/2004 | Chang et al. ................... 502/66 |
| 6,936,744 B1 | 8/2005 | Cheng et al. |
| 2004/0092757 A1 | 5/2004 | Oguchi et al. |
| 2005/0158238 A1 | 7/2005 | Tatsumi et al. |
| 2008/0027256 A1 | 1/2008 | Roth et al. |
| 2008/0027259 A1 | 1/2008 | Roth et al. |
| 2008/0045768 A1 | 2/2008 | Roth et al. |

FOREIGN PATENT DOCUMENTS

| | | |
|---|---|---|
| EP | 0 293 032 | 11/1988 |
| EP | 0 338 734 | 10/1989 |
| WO | 95/31421 | 11/1995 |
| WO | 97/17290 | 5/1997 |
| WO | 01/53236 | 7/2001 |
| WO | 01/74767 | 10/2001 |
| WO | 2005/118476 | 12/2005 |
| WO | 2009/038900 | 3/2009 |

OTHER PUBLICATIONS

I. Borodina et al., "Hydroalkylation of Benzene and Ethylbenzene over Metal Containing Zeolite Catalysts", Microporous and Mesoporous Materials, 2007, vol. 105, pp. 181-188.

(Continued)

Primary Examiner — Sikarl A Witherspoon
(74) Attorney, Agent, or Firm — Jamie Sullivan

(57) ABSTRACT

In a process for producing cyclohexylbenzene, benzene and hydrogen are contacted with a catalyst under hydroalkylation conditions to produce an effluent containing cyclohexylbenzene. The catalyst comprises a composite of a molecular sieve, an inorganic oxide different from said molecular sieve and at least one hydrogenation metal, wherein at least 50 wt % of said hydrogenation metal is supported on the inorganic oxide.

23 Claims, No Drawings

OTHER PUBLICATIONS

W. Fan et al., "*Synthesis and Catalytic Properties of a New Titanosilicate Molecular Sieve with the Structure Analogous to MWW-type Lamellar Precursor*", Journal of Catalyst, 2006, vol. 243, pp. 183-191.

S. Kim et al., "*Structural Evolution of B-MCM-36 and B-ITQ-2 from B-MCM-22*", Bull. Korean Chem. Society, 2006, vol. 27, No. 10, pp. 1693-1696.

S. Lawton et al., "*Zeolite Mcm-49: A Three-Dimensional MCM-22 Analogue Synthesized by in Situ Crystallization*", Journal of Physical Chemistry, 1996, vol. 100, pp. 3788-3798.

S. Maheshwari et al., "*Layer Structure Preservation During Swelling, Pillaring, and Exfoliation of a Zeolite Precursor*", Journal of American Chemical Soc., 2008, vol. 130, pp. 1507-1516.

J. Ruan et al., "*Structure Elucidation of the Highly Active Titanosilicate Catalyst Ti-YNU-1*", Angew. Chem. Int. Ed., 2005, vol. 44, pp. 6719-6723.

L. Slaugh et al., "*Hydrodimerization of Benzene to Phenylcyclohexane over Supported Transition Metal Catalysts*", Journal of Catalysis, 1969, vol. 13, pp. 385-396.

P. Wu et al., "*Methodology for Synthesizing Crystalline Metallosilicates with Expanded Pore Windows Through Molecular Alkoxysilylation of Zeolitic Lamellar Precursors*", Journal of American Chemical Soc., 2008, vol. 130, pp. 8178-8187.

L. Zhicheng et al., "*Static Synthesis of High-Quality MCM-22 Zeolite with High $SiO_2/Al_2O_3$ Ratio*", Chinese Science Bull, 2004, vol. 49, No. 6, pp. 556-561.

\* cited by examiner

PROCESS FOR PRODUCING CYCLOHEXYLBENZENE

PRIORITY CLAIM

This application claims the benefit of prior U.S. provisional application Ser. No. 60/964,874 filed Aug. 15, 2007, and International Patent Cooperation Treaty Application No. PCT/EP2008/006072 filed Jul. 11, 2008, both of which are hereby incorporated by reference in their entirety.

FIELD

The present invention relates to a process for producing cyclohexylbenzene and optionally for converting the resultant cyclohexylbenzene into phenol and cyclohexanone.

BACKGROUND

Phenol is an important product in the chemical industry and is useful in, for example, the production of phenolic resins, bisphenol A, ε-caprolactam, adipic acid, and plasticizers.

Currently, the most common route for the production of phenol is the Hock process. This is a three-step process in which the first step involves alkylation of benzene with propylene to produce cumene, followed by oxidation of the cumene to the corresponding hydroperoxide and then cleavage of the hydroperoxide to produce equimolar amounts of phenol and acetone. However, the world demand for phenol is growing more rapidly than that for acetone. In addition, the cost of propylene is likely to increase, due to a developing shortage of propylene.

Thus, a process that uses higher alkenes instead of propylene as feed and coproduces higher ketones, such as cyclohexanone, rather than acetone may be an attractive alternative route to the production of phenols. For example, there is a growing market for cyclohexanone, which is used as an industrial solvent, as an activator in oxidation reactions and in the production of adipic acid, cyclohexanone resins, cyclohexanone oxime, caprolactam and nylon 6.

It is known from U.S. Pat. No. 5,053,571 that cyclohexylbenzene can be produced by contacting benzene with hydrogen in the presence of a catalyst comprising ruthenium and nickel supported on zeolite beta and that the resultant cyclohexylbenzene can be processed in two steps to cyclohexanone and phenol. The hydroalkylation reaction is carried out at a liquid hourly space velocity (LHSV) ranging from 1 to 100, a reaction pressure ranging from 100 to 1000 kPa, a hydrogen feed rate ranging from 0.2 to 6 mole per mole of feedstock per hour, and a reaction temperature ranging from 100 to 300° C.

In addition, U.S. Pat. No. 5,146,024 discloses that benzene can be reacted with hydrogen in the presence of carbon monoxide and a palladium-containing zeolite X or Y to produce cyclohexylbenzene, which can then be converted in high yield to phenol and cyclohexanone by autooxidation with subsequent acid treatment. The hydroalkylation reaction is carried out at a liquid hourly space velocity (LHSV) of the benzene feed of about 1 to about 100 $hr^{-1}$, a total reaction pressure of about 345 to about 10,350 kPa, a molar ratio of $H_2$ to benzene of about 0.1:1 to about 10:1, a molar ratio of carbon monoxide to $H_2$ of about 0.01:1 to about 0.3:1, and a temperature of about 100 to about 250° C.

Further, U.S. Pat. No. 6,037,513 discloses that cyclohexylbenzene can be produced by contacting benzene with hydrogen in the presence of a bifunctional catalyst comprising a molecular sieve of the MCM-22 family and at least one hydrogenation metal selected from palladium, ruthenium, nickel, cobalt and mixtures thereof. The catalyst may also contain a binder and/or matrix and in the Examples the catalyst is produced by impregnating an extrudate of the MCM-22 family molecular sieve and an alumina binder with an aqueous solution of a salt of the hydrogenation metal using incipient wetness impregnation. The '513 patent also discloses that the resultant cyclohexylbenzene can be oxidized to the corresponding hydroperoxide and the peroxide decomposed to the desired phenol and cyclohexanone.

According to the present invention, it has now been found that the benzene hydroalkylation activity of a bifunctional catalyst comprising a molecular sieve and a hydrogenation metal can be enhanced if some or all of the hydrogenation metal is supported on an inorganic oxide separate from, but composited with, the molecular sieve. Moreover the resultant catalyst exhibits enhanced selectivity to cyclohexylbenzene and dicyclohexylbenzene and reduced selectivity to cyclohexane, which is desirable since any dicyclohexylbenzene can be readily transalkylated with additional benzene to produce further cyclohexylbenzene product.

SUMMARY

In one aspect, the invention resides in a process for producing cyclohexylbenzene, the process comprising contacting benzene and hydrogen with a catalyst under hydroalkylation conditions to produce an effluent containing cyclohexylbenzene, the catalyst comprising a composite of a molecular sieve, an inorganic oxide different from said molecular sieve and at least one hydrogenation metal, wherein at least 50 wt %, such as at least 75 wt %, even substantially all, including as much as 100 wt % of said hydrogenation metal is supported on the inorganic oxide.

In one embodiment, said at least one hydrogenation metal is applied to the inorganic oxide before said inorganic oxide is composited with said molecular sieve.

Conveniently, the catalyst is produced by depositing the at least one hydrogenation metal on the inorganic oxide and then co-pelletizing a mixture of the metal-containing inorganic oxide and the molecular sieve.

Alternatively, the catalyst is produced by depositing the at least one hydrogenation metal on the inorganic oxide and then co-extruding a mixture of the metal-containing inorganic oxide and the molecular sieve. Typically, the mixture further includes a binder.

Conveniently, the molecular sieve has an average pore size of at least 7 Angstrom.

Conveniently, the molecular sieve comprises one or more of zeolite beta, zeolite X, zeolite Y, mordenite or a molecular sieve of the MCM-22 family.

In one embodiment, the molecular sieve is a member of the MCM-22 family and has an X-ray diffraction pattern including d-spacing maxima at 12.4±0.25, 6.9±0.15, 3.57±0.07 and 3.42±0.07 Angstrom. Suitable molecular sieves include MCM-22, PSH-3, SSZ-25, ERB-1, ITQ-1, ITQ-2, MCM-36, MCM-49, MCM-56, UZM-8, and mixtures thereof, and especially MCM-22, MCM-49, MCM-56 and isotypes thereof.

Conveniently, the molecular sieve is an aluminosilicate and in that case the molar ratio of the aluminum in the molecular sieve to the hydrogenation metal is preferably from about 75 to about 750, such as from about 100 to about 300.

Conveniently, the inorganic oxide is an oxide of an element selected from Groups 2, 4, 13 and 14 of the Periodic Table of Elements, such as alumina and/or titania and/or zirconia.

Conveniently, the at least one hydrogenation metal is selected from palladium, ruthenium, nickel, zinc, tin, and cobalt, especially palladium.

Conveniently, the hydroalkylation conditions include a temperature of about 100 to 400° C. and/or a pressure of about 100 to 7000 kPaa. Typically, the molar ratio of hydrogen to benzene in said contacting is in the range of about 0.15:1 to about 15:1.

In one embodiment, the effluent also contains dicyclohexylbenzene and at least part of the dicyclohexylbenzene is contacted with benzene under transalkylation conditions to produce further cyclohexylbenzene.

In a further aspect, the invention resides in a method for coproducing phenol and cyclohexanone, the method comprising producing cyclohexylbenzene by the process described herein, oxidizing the cyclohexylbenzene to produce cyclohexylbenzene hydroperoxide and cleaving the cyclohexylbenzene hydroperoxide to produce phenol and cyclohexanone. In one embodiment of this further aspect, the cyclohexanone is then dehydrogenated to produce further phenol.

DETAILED DESCRIPTION

Described herein is a process for the hydroalkylation of benzene to produce cyclohexylbenzene and then in an optional further stage, the conversion of the cyclohexylbenzene in a two step process to cyclohexanone and phenol. Insofar as the hydroalkylation step produces dicyclohexylbenzene in addition to the desired monocyclohexylbenzene product, the process can include the further step of transalkylating the dicyclohexylbenzene with additional benzene to produce additional monocyclohexylbenzene product.

Benzene Hydroalkylation

The first step in the present process is contacting benzene with hydrogen under hydroalkylation conditions and in the presence of a novel hydroalkylation catalyst whereby the benzene undergoes the following reaction:

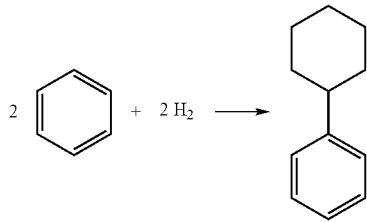

Competing reactions include the complete saturation of the benzene to produce cyclohexane, dialkylation to produce dicyclohexylbenzene and reorganization/alkylation reactions to produce impurities, such as methylcyclopentylbenzene. Although dicyclohexylbenzene can be transalkylated to produce additional monocyclohexylbenzene product, conversion to cyclohexane represents loss of valuable feed, whereas impurities such as methylcyclopentylbenzene (MCPB) are particularly undesirable since the boiling point of MCPB is very close to that of cyclohexylbenzene (CHB) and hence it is very difficult to separate MCPB from CHB, which is the desired product from the hydroalkylation reaction.

Any commercially available benzene feed can be used in the hydroalkylation step, but preferably the benzene has a purity level of at least 99 wt %. Similarly, whereas the source of hydrogen is not critical, it is generally desirable that the hydrogen is at least 99 wt % pure.

Preferably, the total feed to the hydroalkylation step contains less than 1000 ppm, such as less than 500 ppm, water. Preferably, the total feed typically contains less than 100 ppm, such as less than 30 ppm, for example less than 3 ppm, sulfur. Preferably the total feed contains less than 10 ppm, such as less than 1 ppm, for example less than 0.1 ppm, nitrogen. In a particularly preferred embodiment at least two, and preferably, all three of the above mentioned preferred levels for water, sulfur and nitrogen are achieved.

The hydroalkylation reaction can be conducted in a wide range of reactor configurations including fixed bed, slurry reactors, and/or catalytic distillation towers. Suitable reaction temperatures are between about 100° C. and about 400° C., such as between about 125° C. and about 250° C. Suitable reaction pressures are between about 100 and about 7,000 kPaa, such as between about 500 and about 5,000 kPaa. Suitable values for the molar ratio of hydrogen to benzene are between about 0.15:1 and about 15:1, such as between about 0.4:1 and about 4:1.

The novel catalyst employed in the hydroalkylation reaction is a composite of a molecular sieve, an inorganic oxide different from the molecular sieve and a hydrogenation metal, in which at least 50 wt % of the hydrogenation metal is supported on the inorganic oxide rather than on the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

Generally, the molecular sieve employed in the present hydroalkylation process has an average pore size of at least 7 Angstrom and conveniently is selected from the group consisting of zeolite beta, zeolite X, zeolite Y, mordenite and a molecular sieve of the MCM-22 family. Zeolite beta and its synthesis are disclosed in, for example, U.S. Pat. No. 3,308,069.

The term "MCM-22 family material" (or "material of the MCM-22 family" or "molecular sieve of the MCM-22 family"), as used herein, includes one or more of:

- molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);
- molecular sieves made from a common second degree building block, being a 2-dimensional tiling of such MWW framework topology unit cells, forming a monolayer of one unit cell thickness, preferably one c-unit cell thickness;
- molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and
- molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom.

The X-ray diffraction data used to characterize the materials are obtained by standard techniques such as using the K-alpha doublet of copper as the incident radiation and a diffractometer equipped with a scintillation counter and associated computer as the collection system.

Molecular sieves of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures of any two or more thereof. Preferably, the molecular sieve is selected from (a) MCM-49, (b) MCM-56 and (c) isotypes of MCM-49 and MCM-56, such as ITQ-2.

The inorganic oxide employed in the hydroalkylation catalyst is not narrowly defined provided it is stable and inert under the conditions of the hydroalkylation reaction. Suitable inorganic oxides include oxides of elements of Groups 2, 4, 13 and 14 of the Periodic Table of Elements, such as alumina, titania and zirconia. As used herein, the numbering scheme for the Periodic Table Groups is as disclosed in Chemical and Engineering News, 63(5), 27 (1985).

Similarly, any known hydrogenation metal can be employed in the catalyst composite although suitable metals include palladium, ruthenium, nickel, zinc, tin, and cobalt, with palladium being particularly advantageous. Generally, the amount of hydrogenation metal present in the catalyst is between about 0.05 and about 10 wt %, such as between about 0.1 and about 5 wt %, of the catalyst. In one embodiment, where the molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal is present in the composite catalyst such that at least 50 wt %, for example at least 75 wt %, and preferably substantially all, even 100 wt %, of the hydrogenation metal is supported on the inorganic oxide. This is conveniently achieved by depositing at least part, and preferably substantially all, of the hydrogenation metal on the inorganic oxide before the metal-containing inorganic oxide is composited with said molecular sieve. If necessary, additional hydrogenation metal can subsequently be deposited on the resultant catalyst composite. Typically, the catalyst composite is produced by co-pelletization, in which a mixture of the molecular sieve and the inorganic oxide are formed into pellets at high pressure (generally about 350 to about 350,000 kPa), or by co-extrusion, in which a mixture, for example a slurry, of the molecular sieve and the inorganic oxide, optionally together with a separate binder, are forced through a die.

Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. It will be understood that the separate binder as referred to above is different from the inorganic oxide that is a necessary component of the composite catalyst in that the oxide carries the catalyst metal (at least 50 wt % thereof) whereas the separate binder does not.

Although the hydroalkylation step is highly selective towards cyclohexylbenzene, the effluent from the hydroalkylation reaction will normally contain some dialkylated products, as well as unreacted aromatic feed and the desired monoalkylated species. The unreacted aromatic feed is normally recovered by distillation and recycled to the alkylation reactor. The bottoms from the benzene distillation are further distilled to separate the monocyclohexylbenzene product from any dicyclohexylbenzene and other heavies. Depending on the amount of dicyclohexylbenzene present in the reaction effluent, it may be desirable to transalkylate the dicyclohexylbenzene with additional benzene to maximize the production of the desired monoalkylated species.

Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y or mordenite. The transalkylation reaction is typically conducted under at least partial liquid phase conditions, which suitably include a temperature of about 100 to about 300° C. Preferably, the transalkylation is carried out at a pressure of about 800 to about 3500 kPa and/or a weight hourly space velocity of about 1 to about 10 $hr^{-1}$ on total feed and/or a benzene/dicyclohexylbenzene weight ratio about of 1:1 to about 5:1.

Cyclohexylbenzene Oxidation

In order to convert the cyclohexylbenzene into phenol and cyclohexanone, the cyclohexylbenzene is initially oxidized to the corresponding hydroperoxide. This is accomplished by introducing an oxygen-containing gas, such as air, into a liquid phase containing the cyclohexylbenzene. Unlike cumene, atmospheric air oxidation of cyclohexylbenzene in the absence of a catalyst is very slow and hence the oxidation is normally conducted in the presence of a catalyst.

Suitable catalysts for the cyclohexylbenzene oxidation step are the N-hydroxy substituted cyclic imides described in U.S. Pat. No. 6,720,462 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide. Preferably, the catalyst is N-hydroxyphthalimide. Another suitable catalyst is N,N',N''-thihydroxyisocyanuric acid.

These materials can be used either alone or in the presence of a free radical initiator and can be used as liquid-phase, homogeneous catalysts or can be supported on a solid carrier to provide a heterogeneous catalyst. Typically, the N-hydroxy substituted cyclic imide or the N,N',N''-trihydroxyisocyanuric acid is employed in an amount between 0.0001 wt % to 15 wt %, such as between 0.001 to 5 wt %, of the cyclohexylbenzene.

Suitable conditions for the oxidation step include a temperature between about 70° C. and about 200° C., such as about 90° C. to about 130° C. and/or a pressure of about 50 to 10,000 kPa. Any oxygen-containing gas, preferably air, can be used as the oxidizing medium. The reaction can take place in batch reactors or continuous flow reactors. A basic buffering agent may be added to react with acidic by-products that may form during the oxidation. In addition, an aqueous phase may be introduced, which can help dissolve basic compounds, such as sodium carbonate.

Hydroperoxide Cleavage

The final reactive step in the conversion of the cyclohexylbenzene into phenol and cyclohexanone involves cleavage of the cyclohexylbenzene hydroperoxide, which is conveniently effected by contacting the hydroperoxide with a catalyst in the liquid phase. The contact is preferably at a temperature of about 20° C. to about 150° C., such as about 40° C. to about 120° C. The pressure is preferably from about 50 to about 2,500 kPa, such as about 100 to about 1000 kPa. The cyclohexylbenzene hydroperoxide is preferably diluted in an organic solvent inert to the cleavage reaction, such as methyl ethyl ketone, cyclohexanone, phenol or cyclohexylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid, with preferred concentrations in the range of 0.05 to 0.5 wt %. For a homogeneous acid catalyst, a neutralization step preferably follows the cleavage step. Such a neutralization step typically involves contact with a basic component, with subsequent decanting of a salt-enriched aqueous phase.

A suitable heterogeneous catalyst for use in the cleavage of cyclohexylbenzene hydroperoxide includes a smectite clay, such as an acidic montmorillonite silica-alumina clay, as described in U.S. Pat. No. 4,870,217, the entire disclosure of which is incorporated herein by reference.

The crude cyclohexanone and crude phenol from the cleavage step may be subjected to further purification to produce purified cyclohexanone and/or purified phenol. A suitable purification process includes, but is not limited to, a series of distillation towers to separate the cyclohexanone and phenol from other species. The crude or purified cyclohexanone may itself be subjected to dehydrogenation in order to convert it to phenol. Such dehydrogenation may be performed, for example, over a catalyst such as platinum, nickel or palladium.

The following Example is given for illustrative purposes and does not limit the scope of the invention.

EXAMPLE

To illustrate the importance of the location of the hydrogenation metal in hydroalkylation, Table 1 below compares the performance of two catalysts, A and B, containing the same amount of palladium but with the palladium being either on the molecular sieve (catalyst A) or an inorganic oxide support (catalyst B). Both catalysts contained 0.006 g Pd and 1.6 g MCM-49 with catalyst A containing 0.4 g of a gamma alumina support and with catalyst B containing 2.0 g of a gamma alumina support.

Catalyst A was prepared by depositing palladium onto MCM-49 zeolite by an incipient wetness technique. The gamma alumina was then added to the Pd-impregnated MCM-49 to form a mixture. The mixture was then pelletized using a hand press under 136,000 kPaa for 60 seconds to form a pellet. The pellet was then sized to particles that passed through 0.841 mm openings but not through 0.250 mm openings (20/60 mesh particles) before it was tested for its benzene hydroalkylation performance. With catalyst A, all the palladium is on the molecular sieve.

Catalyst B was prepared by first depositing palladium onto the gamma alumina. The Pd-containing gamma alumina was then added to MCM-49 to form a mixture. The mixture was then pelletized using a hand press under 136,000 kPaa for 60 seconds. The pellet was then sized to particles that passed through 0.841 mm openings but not through 0.25 mm openings (20/60 mesh particles) before it was tested for its benzene hydroalkylation performance. With catalyst B, all the palladium is on the inorganic oxide.

The catalysts were tested at a temperature of 150° C. and a pressure of 1034 kPag (150 psig) with a feed comprising 0.08 cc/min benzene and 10 cc/min hydrogen. The results are summarized in Table 1.

TABLE 1

| | Catalyst | |
| --- | --- | --- |
| | A | B |
| | Hydrogenation Metal Location | |
| | Zeolite | Inorganic oxide |
| Conversion, % | 36.9 | 43.5 |
| Selectivity, % | | |
| Cyclohexane | 12.1 | 7.1 |
| Cyclohexylbenzene | 69.9 | 70.8 |
| Dicyclohexylbenzene | 14.9 | 17.3 |
| Others | 3.1 | 4.8 |

As can be seen from Table 1, the performance of catalyst B is superior to that of catalyst A. The conversion of catalyst B is 43.5 wt % as compared with 36.9 wt % for catalyst A. Further, the total selectivity towards cyclohexylbenzene and dicyclohexylbenzene is nearly 88 wt % for catalyst B which is significantly higher than the 85% selectivity shown by catalyst A. The Table illustrates the importance of having the hydrogenation metal on the inorganic oxide.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing cyclohexylbenzene, the process comprising contacting benzene and hydrogen with a catalyst under hydroalkylation conditions to produce an effluent containing cyclohexylbenzene, the catalyst comprising a composite of a molecular sieve, an inorganic oxide different from said molecular sieve and at least one hydrogenation metal, wherein at least 50 wt % of said hydrogenation metal is supported on the inorganic oxide, wherein the molecular sieve is an aluminosilicate and the molar ratio of the aluminum in the molecular sieve to the hydrogenation metal is from 1.5 to 1500.

2. The process of claim 1, wherein at least 75 wt % of the hydrogenation metal is supported on the inorganic oxide.

3. The process of claim 1, wherein substantially all of the hydrogenation metal is supported on the inorganic oxide.

4. The process of claim 1, wherein the at least one hydrogenation metal is applied to the inorganic oxide before the inorganic oxide is composited with the molecular sieve.

5. The process of claim 4, wherein the catalyst is produced by depositing the at least one hydrogenation metal on the inorganic oxide and then co-pelletizing a mixture of the metal-containing inorganic oxide and the molecular sieve.

6. The process of claim 4, wherein the catalyst is produced by depositing the at least one hydrogenation metal on the inorganic oxide and then co-extruding a mixture of the metal-containing inorganic oxide and the molecular sieve.

7. The process of claim 6, wherein the mixture further includes a binder.

8. The process of claim 1, wherein the molecular sieve has an average pore size of at least 7 Angstrom.

9. The process of claim 1, wherein the molecular sieve is selected from zeolite beta, zeolite X, zeolite Y, mordenite and molecular sieves of the MCM-22 family.

10. The process of claim 1, wherein the molecular sieve is of the MCM-22 family and has an X-ray diffraction pattern including d-spacing maxima at 12.4±0.25, 6.9±0.15, 3.57±0.07 and 3.42±0.07 Angstrom.

11. The process of claim 1, wherein the molecular sieve is selected from MCM-22, PSH-3, SSZ-25, ERB-1, ITQ-1, ITQ-2, MCM-36, MCM-49, MCM-56, UZM-8, and combinations of any two or more thereof.

12. The process of claim 1, wherein the molecular sieve is selected from MCM-22, MCM-49, MCM-56 and combinations of any two or more thereof.

13. The process of claim 1, wherein the molar ratio of the aluminum in the molecular sieve to the hydrogenation metal is from 100 to 300.

14. The process of claim 1, wherein the inorganic oxide comprises an oxide of at least one element of Groups 2, 4, 13 and 14 of the Periodic Table of Elements.

15. The process of claim 1, wherein the inorganic oxide comprises alumina and/or titania and/or zirconia.

16. The process of claim 1, wherein the or one of the said at least one hydrogenation metal is selected from palladium, ruthenium, nickel, zinc, tin, and cobalt.

17. The process of claim 1, wherein the or one of the said at least one hydrogenation metal comprises palladium.

18. The process of claim 1, wherein the molar ratio of hydrogen to benzene in said contacting is in the range 0.15:1 to 15:1.

19. The process of claim 1, wherein the hydroalkylation conditions include a temperature of from 100 to 400° C. and/or a pressure of from 100 to 7000 kPaa.

20. The process of claim 1, wherein the effluent also contains dicyclohexylbenzene and at least part of the dicyclohexylbenzene is contacted with benzene under transalkylation conditions to produce further cyclohexylbenzene.

21. A method for coproducing phenol and cyclohexanone, the method comprising producing cyclohexylbenzene by the process of claim 1, oxidizing the cyclohexylbenzene to produce cyclohexylbenzene hydroperoxide and cleaving the cyclohexylbenzene hydroperoxide to produce phenol and cyclohexanone.

22. The process of claim 21 which further comprises dehydrogenating the cyclohexanone to produce further phenol.

23. A process for producing cyclohexylbenzene, the process comprising contacting benzene and hydrogen with a catalyst under hydroalkylation conditions to produce an effluent containing cyclohexylbenzene, the catalyst comprising a composite of a molecular sieve, an inorganic oxide different from said molecular sieve and at least one hydrogenation metal, wherein at least 50 wt % of said hydrogenation metal is supported on the inorganic oxide, and wherein the at least one hydrogenation metal is applied to the inorganic oxide before the inorganic oxide is composited with the molecular sieve.

* * * * *